United States Patent
Kharin (12) United States Patent (10) Patent No.: US 10,905,901 B2
(45) Date of Patent: *Feb. 2, 2021

(54) ULTRASOUND DEVICE FOR PRECISE TISSUE SEALING AND BLADE-LESS CUTTING

(71) Applicant: COVIDIEN LP, Mansfield, MA (US)

(72) Inventor: Nikolay Kharin, Loveland, CO (US)

(73) Assignee: COVIDIEN LP, Mansfield, MA (US)

( * ) Notice: Subject to any disclaimer, the term of this patent is extended or adjusted under 35 U.S.C. 154(b) by 494 days.

This patent is subject to a terminal disclaimer.

(21) Appl. No.: 15/809,304

(22) Filed: Nov. 10, 2017

(65) Prior Publication Data

US 2018/0064964 A1   Mar. 8, 2018

Related U.S. Application Data (63) Continuation of application No. 14/604,283, filed on Jan. 23, 2015, now Pat. No. 9,814,910, which is a continuation of application No. 13/111,678, filed on May 19, 2011, now Pat. No. 8,968,283.

(51) Int. Cl.
  *A61N 7/00* (2006.01)
  *A61B 17/32* (2006.01)
  *A61B 18/14* (2006.01)

(52) U.S. Cl.
  CPC ............ *A61N 7/00* (2013.01); *A61B 18/1445* (2013.01); *A61B 2017/320093* (2017.08); *A61B 2017/320094* (2017.08); *A61B 2017/320095* (2017.08); *A61N 2007/0078* (2013.01)

(58) Field of Classification Search
  CPC .... A61B 18/1445; A61B 2017/320093; A61B 2017/320094; A61B 2017/320095; A61N 2007/0078; A61N 7/00
  See application file for complete search history.

(56) References Cited

U.S. PATENT DOCUMENTS

| D249,549 S | 9/1978 | Pike |
| D263,020 S | 2/1982 | Rau, III |
| D295,893 S | 5/1988 | Sharkany et al. |

(Continued)

FOREIGN PATENT DOCUMENTS

| CN | 201299462 Y | 9/2009 |
| DE | 2415263 A1 | 10/1975 |

(Continued)

OTHER PUBLICATIONS

"Electrosurgery: A Historical Overview" Innovations in Electrosurgery; Sales/Product Literature; Dec. 31, 2000.

(Continued)

*Primary Examiner* — Michael F Peffley
(74) *Attorney, Agent, or Firm* — Carter, DeLuca & Farrell LLP (57) ABSTRACT

An electrosurgical instrument for sealing and cutting tissue is provided. The instrument includes a housing having a plurality of transducers included therein and a waveguide coupled to and extending from the housing. An end effector assembly disposed at a distal end of the waveguide includes a pair of opposing jaw members, where at least one of the jaw members includes a transducer. The transducer is configured to receive an acoustic signal from the plurality of transducers in the housing.

14 Claims, 6 Drawing Sheets

(56) References Cited

U.S. PATENT DOCUMENTS

| | | | |
|---|---|---|---|
| D295,894 S | 5/1988 | Sharkany et al. | |
| D298,353 S | 11/1988 | Manno | |
| D299,413 S | 1/1989 | DeCarolis | |
| D343,453 S | 1/1994 | Noda | |
| D348,930 S | 7/1994 | Olson | |
| D349,341 S | 8/1994 | Lichtman et al. | |
| D354,564 S | 1/1995 | Medema | |
| D358,887 S | 5/1995 | Feinberg | |
| D384,413 S | 9/1997 | Zlock et al. | |
| 5,728,089 A * | 3/1998 | Lal | A61B 18/1402 606/1 |
| H001745 H | 8/1998 | Paraschac | |
| D402,028 S | 12/1998 | Grimm et al. | |
| D408,018 S | 4/1999 | McNaughton | |
| D416,089 S | 11/1999 | Barton et al. | |
| D424,694 S | 5/2000 | Tetzlaff et al. | |
| D425,201 S | 5/2000 | Tetzlaff et al. | |
| H001904 H | 10/2000 | Yates et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H002037 H | 7/2002 | Yates et al. | |
| D465,281 S | 11/2002 | Lang | |
| D466,209 S | 11/2002 | Bon | |
| 6,680,613 B2 | 1/2004 | Rosthal et al. | |
| D493,888 S | 8/2004 | Reschke | |
| 6,773,409 B2 | 8/2004 | Truckai et al. | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al. | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| 7,491,201 B2 * | 2/2009 | Shields | A61B 18/1445 606/51 |
| 7,587,291 B1 | 9/2009 | Sarvazyan et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| 8,292,888 B2 * | 10/2012 | Whitman | A61B 18/1442 606/51 |
| 8,968,283 B2 | 3/2015 | Kharin | |
| 9,814,910 B2 | 11/2017 | Kharin | |
| 2002/0183774 A1 * | 12/2002 | Witt | A61B 17/320092 606/169 |
| 2004/0054364 A1 | 3/2004 | Aranyi et al. | |
| 2009/0036914 A1 * | 2/2009 | Houser | A61B 17/320068 606/169 |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 A1 | 3/1999 |
| DE | 19751108 A1 | 5/1999 |
| DE | 10045375 A1 | 4/2002 |
| DE | 102004026179 A1 | 12/2005 |
| DE | 202007009165 U1 | 8/2007 |
| DE | 202007009317 U1 | 10/2007 |
| DE | 202007016233 U1 | 1/2008 |
| DE | 102008018406 B3 | 7/2009 |
| EP | 1159926 A3 | 3/2003 |
| JP | 61501068 | 9/1984 |
| JP | 1024051 | 1/1989 |
| JP | 6502328 | 3/1992 |
| JP | 55106 | 1/1993 |
| JP | 0540112 | 2/1993 |
| JP | 6121797 | 5/1994 |
| JP | 6285078 | 10/1994 |
| JP | 06343644 A | 12/1994 |
| JP | 6511401 | 12/1994 |
| JP | 07265328 A | 10/1995 |
| JP | 856955 | 5/1996 |
| JP | 08252263 A | 10/1996 |
| JP | 8317934 | 12/1996 |
| JP | 910223 | 1/1997 |
| JP | 9122138 | 5/1997 |
| JP | 10155798 | 6/1998 |
| JP | 1147150 | 2/1999 |
| JP | 11070124 | 3/1999 |
| JP | 11169381 | 6/1999 |
| JP | 11192238 | 7/1999 |
| JP | 11244298 A | 9/1999 |
| JP | 2000102545 A | 4/2000 |
| JP | 2000342599 A | 12/2000 |
| JP | 2000350732 A2 | 12/2000 |
| JP | 20018944 | 1/2001 |
| JP | 200129356 | 2/2001 |
| JP | 2001128990 A | 5/2001 |
| JP | 2001190564 A | 7/2001 |
| JP | 2004517668 A | 6/2004 |
| JP | 2004528869 A | 9/2004 |
| SU | 401367 A1 | 10/1973 |
| WO | 0036986 A1 | 6/2000 |
| WO | 0115614 A1 | 3/2001 |
| WO | 0154604 A1 | 8/2001 |
| WO | 05110264 A3 | 4/2006 |

OTHER PUBLICATIONS

Johnson et al. "Evaluation of a Bipolar Electrothermal Vessel Sealing Device in Hemorrhoidectomy" Sales/Product Literature; Jan. 2004.

E. David Crawford "Evaluation of a New Vessel Sealing Device in Urologic Cancer Surgery" Sales/Product Literature 2000.

Johnson et al. "Evaluation of the LigaSure Vessel Sealing System in Hemorrhoidectormy" American College of Surgeons (ACS) Clinicla Congress Poster (2000).

Muller et al., "Extended Left Hemicolectomy Using the LigaSure Vessel Sealing System" Innovations That Work, Sep. 1999.

Kennedy et al. "High-burst-strength, feedback-controlled bipolar vessel sealing" Surgical Endoscopy (1998) 12: 876-878.

Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.

(56) References Cited

OTHER PUBLICATIONS

Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
U.S. Appl. No. 08/926,869, filed Sep. 10, 1997, James G. Chandler.
U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremeich.
U.S. Appl. No. 12/692,414, filed Jan. 22, 2010, Peter M. Mueller.
U.S. Appl. No. 12/696,592, filed Jan. 29, 2010, Jennifer S. Harper.
U.S. Appl. No. 12/696,857, filed Jan. 29, 2010, Edward M. Chojin.
U.S. Appl. No. 12/700,856, filed Feb. 5, 2010, James E. Krapohl.
U.S. Appl. No. 12/719,407, filed Mar. 8, 2010, Arlen J. Reschke.
U.S. Appl. No. 12/728,994, filed Mar. 22, 2010, Edward M. Chojin.
U.S. Appl. No. 12/748,028, filed Mar. 26, 2010, Jessica E.C. Olson.
U.S. Appl. No. 12/757,340, filed Apr. 9, 2010, Carine Hoarau.
U.S. Appl. No. 12/758,524, filed Apr. 12, 2010, Duane E. Kerr.
U.S. Appl. No. 12/759,551, filed Apr. 13, 2010, Glenn A. Homer.
U.S. Appl. No. 12/769,444, filed Apr. 28, 2010, Glenn A. Nomer.
U.S. Appl. No. 12/770,369, filed Apr. 29, 2010, Glenn A. Homer.
U.S. Appl. No. 12/770,380, filed Apr. 29, 2010, Glenn A. Homer.
U.S. Appl. No. 12/770,387, filed Apr. 29, 2010, Glenn A. Homer.
U.S. Appl. No. 12/773,526, filed May 4, 2010, Duane E. Kerr.
U.S. Appl. No. 12/773,644, filed May 4, 2010, Thomas J. Gerhardt.
U.S. Appl. No. 12/786,589, filed May 25, 2010, Duane E. Kerr.
U.S. Appl. No. 12/791,112, filed Jun. 1, 2010, David M. Garrison.
U.S. Appl. No. 12/792,001, filed Jun. 2, 2010, Duane E. Kerr.
U.S. Appl. No. 12/792,008, filed Jun. 2, 2010, Duane E. Kerr.
U.S. Appl. No. 12/792,019, filed Jun. 2, 2010, Duane E. Kerr.
U.S. Appl. No. 12/792,038, filed Jun. 2, 2010, Glenn A. Homer.
U.S. Appl. No. 12/792,051, filed Jun. 2, 2010, David M. Garrison.
U.S. Appl. No. 12/792,068, filed Jun. 2, 2010, Glenn A. Homer.
U.S. Appl. No. 12/792,097, filed Jun. 2, 2010, Duane E. Kerr.
U.S. Appl. No. 12/792,262, filed Jun. 2, 2010, Jeffrey M. Roy.
U.S. Appl. No. 12/792,299, filed Jun. 2, 2010, Jeffrey M. Roy.
U.S. Appl. No. 12/792,330, filed Jun. 2, 2010, David M. Garrison.
U.S. Appl. No. 12/822,024, filed Jun. 23, 2010, Peter M. Mueller.
U.S. Appl. No. 12/821,253, filed Jun. 23, 2010, Edward M. Chojin.
U.S. Appl. No. 12/832,772, filed Jul. 8, 2010, Gary M. Couture.
U.S. Appl. No. 12/843,384, filed Jul. 26, 2010, David M. Garrison.
U.S. Appl. No. 12/845,203, filed Jul. 28, 2010, Gary M. Couture.
U.S. Appl. No. 12/853,896, filed Aug. 10, 2010, William H. Nau, Jr.
U.S. Appl. No. 12/859,896, filed Aug. 20, 2010, Peter M. Mueller.
U.S. Appl. No. 12/861,198, filed Aug. 23, 2010, James A. Gilbert.
U.S. Appl. No. 12/861,209, filed Aug. 23, 2010, William H. Nau, Jr.
U.S. Appl. No. 12/876,668, filed Sep. 7, 2010, Sara E. Anderson.

(56) References Cited

OTHER PUBLICATIONS

U.S. Appl. No. 12/876,680, filed Sep. 7, 2010, Peter M. Mueller.
U.S. Appl. No. 12/876,705, filed Sep. 7, 2010, Kristin D. Johnson.
U.S. Appl. No. 12/876,731, filed Sep. 7, 2010, Kristin D. Johnson.
U.S. Appl. No. 12/877,199, filed Sep. 8, 2010, Arlen J. Reschke.
U.S. Appl. No. 12/877,482, filed Sep. 8, 2010, Gary M. Couture.
U.S. Appl. No. 12/895,020, filed Sep. 30, 2010, Jeffrey M. Roy.
U.S. Appl. No. 12/896,100, filed Oct. 1, 2010, Ryan Artale.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 185386.9 dated Jan. 10, 2011.
Int'l Search Report EP 10 185405.7 dated Jan. 5, 2011.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
U.S. Appl. No. 12/897,346, filed Oct. 4, 2010, Ryan Artale.
U.S. Appl. No. 12/906,672, filed Oct. 18, 2010, Kathy E. Rooks.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/006,538, filed Jan. 14, 2011, John W. Twomey.
U.S. Appl. No. 13,029,390, filed Feb. 17, 2011, Michael C. Moses.
U.S. Appl. No. 13/030,231, filed Feb. 18, 2011, Jeffrey M. Roy.
U.S. Appl. No. 13/050,182, filed Mar. 17, 2011, Glenn A. Homer.
U.S. Appl. No. 13/072,945, filed Mar. 28, 2011, Patrick L. Dumbauld.
U.S. Appl. No. 13/075,847, filed Mar. 30, 2011, Gary M. Couture.
U.S. Appl. No. 13/080,383, filed Apr. 5, 2011, David M. Garrison.
U.S. Appl. No. 13/083,962, filed Apr. 11, 2011, Michael C. Moses.
U.S. Appl. No. 13/085,144, filed Apr. 12, 2011, Keir Hart.
U.S. Appl. No. 13/089,779, filed Apr. 19, 2011, Yevgeniy Fedotov.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
Michael Choti, "Abdominoperineal Resection with the LigaSure Vessel Sealing System and LigaSure Atlas 20 cm Open Instrument"; Innovations That Work, Jun. 2003.

(56) References Cited

OTHER PUBLICATIONS

Chung et al., "Clinical Experience of Sutureless Closed Hemorrhoidectomy with LigaSure" Diseases of the Colon & Rectum vol. 46, No. Jan. 1, 2003.
Tinkcler L.F., "Combined Diathermy and Suction Forceps", Feb. 6, 1967 (Feb. 6, 1965), British Medical Journal Feb. 6, 1976, vol. 1, No. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.
Peterson et al. "Comparison of Healing Process Following Ligation with Sutures and Bipolar Vessel Sealing" Surgical Technology International (2001).

\* cited by examiner

ULTRASOUND DEVICE FOR PRECISE TISSUE SEALING AND BLADE-LESS CUTTING

CROSS-REFERENCE TO RELATED APPLICATIONS

This application is a continuation of U.S. patent application Ser. No. 14/604,283, filed Jan. 23, 2015, which is a continuation of U.S. patent application Ser. No. 13/111,678, filed May 19, 2011, now U.S. Pat. No. 8,968,283. The entire contents of each of the above applications are hereby incorporated by reference.

BACKGROUND

1. Technical Field

The present disclosure is directed to an electrosurgical apparatus. More specifically, the present disclosure is directed to an electrosurgical apparatus that employs ultrasound for precise tissue sealing and blade-less cutting.

2. Background of the Related Art

Open or endoscopic electrosurgical forceps utilize both mechanical clamping action and electrical energy to effect hemostasis. The electrode of each opposing jaw member is charged to a different electric potential such that when the jaw members grasp tissue, electrical energy can be selectively transferred through the tissue. A surgeon can cauterize, coagulate/desiccate and/or simply reduce or slow bleeding, by controlling the intensity, frequency and duration of the electrosurgical energy applied between the electrodes and through the tissue.

Certain surgical procedures require more than simply cauterizing tissue and rely on the combination of clamping pressure, electrosurgical energy and gap distance to "seal" tissue, vessels and certain vascular bundles. More particularly, vessel sealing or tissue sealing utilizes a unique combination of radiofrequency (RF) energy, clamping pressure and precise control of gap distance (i.e., distance between opposing jaw members when closed about tissue) to effectively seal or fuse tissue between two opposing jaw members or sealing plates. Vessel or tissue sealing is more than "cauterization", which involves the use of heat to destroy tissue (also called "diathermy" or "electrodiathermy"). Vessel sealing is also more than "coagulation", which is the process of desiccating tissue wherein the tissue cells are ruptured and dried. "Vessel sealing" is defined as the process of liquefying the collagen, elastin and ground substances in the tissue so that the tissue reforms into a fused mass with significantly-reduced demarcation between the opposing tissue structures.

Many electrosurgical instruments include a cutting member for cutting sealed tissue. Existing methods involve the use mechanical or electrical cutting actions. For example, a knife may be included in an electrosurgical instrument. Alternatively, an electrode may be used to apply electrical energy in the region. The use of a knife or electrode may be disadvantageous because it may lead to uncontrollable wide thermal spread.

Ultrasound may also be used for sealing and cutting tissue. One such example is an ultrasonic scalpel that uses an acoustic transducer operating in a longitudinal mode at 55 KHz located remotely from tissue. Energy is amplified and transmitted to the blade system by an acoustic mount coupled to the housing of a hand piece. Mechanical energy propagates in a metallic rod of the blade system having jaw members at a distal end thereof. However, such a device can not concentrate ultrasound waves in a precise spot and, as a result, may have an even larger thermal spread then many radio frequency electrosurgical devices.

SUMMARY

In an embodiment of the present disclosure, an electrosurgical instrument for sealing and cutting tissue is provided. The instrument includes a housing having a plurality of transducers included therein and a waveguide coupled to and extending from the housing. An end effector assembly disposed at a distal end of the waveguide includes a pair of opposing jaw members, where at least one of the jaw members includes a transducer. The transducer is configured to receive an acoustic signal from the plurality of transducers in the housing.

The transducer in the end effector assembly is coupled to a generator and the transducer converts the received acoustic signal into an electrical signal that is transmitted to the generator. The generator receives the electrical signal and outputs a time-reversed signal to the plurality of transducers in the housing. The plurality of transducers in the housing transmits the time-reversed signal to the transducer in the end effector assembly through the waveguide.

The transducer in the end effector assembly may be a piezoceramic transducer that is formed beneath a sealing surface of the at least one jaw member, as an integral part of a sealing surface of the at least one jaw member or formed as a stop member on top of a sealing surface of the at least one jaw member.

In another embodiment of the present disclosure, an electrosurgical system is provided. The system includes an electrosurgical instrument having a housing with a plurality of transducers included therein and a waveguide coupled to and extending from the housing. An end effector assembly disposed at a distal end of the waveguide includes a pair of opposing jaw members, where at least one of the jaw members includes a transducer. The transducer is configured to receive an acoustic signal from the plurality of transducers in the housing. The system also includes a generator coupled to the plurality of transducers in the housing and the transducer in the end effector assembly.

The transducer in the end effector assembly converts the received acoustic signal from the plurality of transducers in the housing into an electrical signal that is transmitted to the generator. The generator includes a phase/time reversal unit configured to receive the electrical signal from the transducer in the end effector assembly and output a reversed electrical signal to the plurality of transducers in the housing.

The transducer in the end effector assembly may be a piezoceramic transducer that is formed beneath a sealing surface of the at least one jaw member, as an integral part of a sealing surface of the at least one jaw member or formed as a stop member on top of a sealing surface of the at least one jaw member.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Particular embodiments of the present disclosure are described hereinbelow with reference to the accompanying drawings; however, the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Like reference numerals may refer to similar or identical elements throughout the description of the figures. As shown in the drawings and described throughout the following description, as is traditional when referring to relative positioning on a surgical instrument, the term "proximal" refers to the end of the apparatus that is closer to the user and the term "distal" refers to the end of the apparatus that is farther away from the user. The term "clinician" refers to any medical professional (e.g., doctor, surgeon, nurse, or the like) performing a medical procedure involving the use of embodiments described herein.

Electromagnetic energy is generally classified by increasing energy or decreasing wavelength into radio waves, microwaves, infrared, visible light, ultraviolet, X-rays and gamma-rays. As used herein, the term "microwave" generally refers to electromagnetic waves in the frequency range of 300 megahertz (MHz) ($3 \times 10^8$ cycles/second) to 300 gigahertz (GHz) ($3 \times 10^{11}$ cycles/second). As used herein, the term "RF" generally refers to electromagnetic waves having a lower frequency than microwaves. As used herein, the term "ultrasound" generally refers to cyclic sound pressure with a frequency greater than the upper limit of human hearing. The terms "tissue" and "vessel" may be used interchangeably since it is believed that the present disclosure may be employed to seal and cut tissue or seal and cut vessels utilizing the same principles described herein.

Figure 1A:
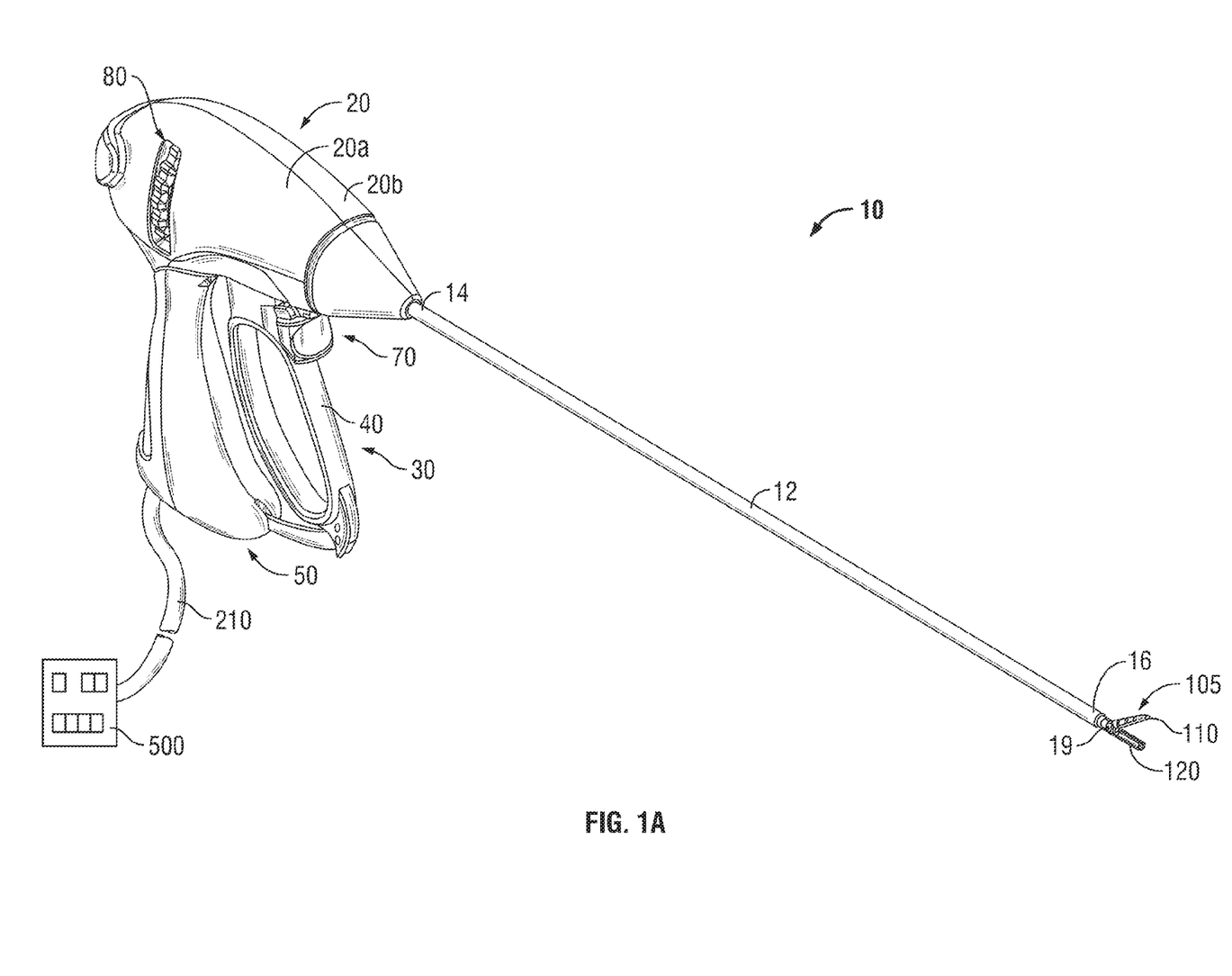
FIG. 1A is a right, perspective view of an electrosurgical instrument according to an embodiment of the present disclosure.

FIG. 1 depicts a bipolar forceps 10 for use with various endoscopic surgical procedures and generally includes a housing 20, a handle assembly 30, a rotating assembly 80, a switch assembly 70 and an end effector assembly 105 having opposing jaw members 110 and 120 that mutually cooperate to grasp, seal and/or divide tubular vessels and vascular tissue. The jaw members 110 and 120 are connected about pivot pin 19, which allows the jaw members 110 and 120 to pivot relative to one another from the first to second positions for treating tissue.

Forceps 10 may be a unilateral or bilateral forceps that includes a waveguide 12 that has a distal end 16 configured to mechanically engage the end effector assembly 105 and a proximal end 14 that mechanically engages the housing 20. The waveguide 12 may include one or more known mechanically-engaging components that are designed to securely receive and engage the end effector assembly 105 such that the jaw members 110 and 120 are pivotable relative to one another to engage and grasp tissue therebetween. The proximal end 14 of waveguide 12 mechanically engages the rotating assembly 80 to facilitate rotation of the end effector assembly 105.

Handle assembly 30 includes a fixed handle 50 and a movable handle 40. Fixed handle 50 is integrally associated with housing 20 and handle 40 is movable relative to fixed handle 50 to actuate the opposing jaw members 110 and 120 of the end effector assembly 105. Movable handle 40 and switch assembly 70 are of unitary construction and are operatively connected to the housing 20 and the fixed handle 50 during the assembly process. Housing 20 is constructed from two component halves 20a and 20b that are assembled about the proximal end of waveguide 12 during assembly. Switch assembly 70 is configured to selectively provide ultrasound to the end effector assembly 105 via waveguide 12 as will be described in more detail below.

As mentioned above, end effector assembly 105 is attached to the distal end 16 of waveguide 12 and includes the opposing jaw members 110 and 120. Movable handle 40 of handle assembly 30 imparts movement of the jaw members 110 and 120 from an open position wherein the jaw members 110 and 120 are disposed in spaced relation relative to one another, to a clamping or closed position wherein the jaw members 110 and 120 cooperate to grasp tissue therebetween.

Figure 1B:
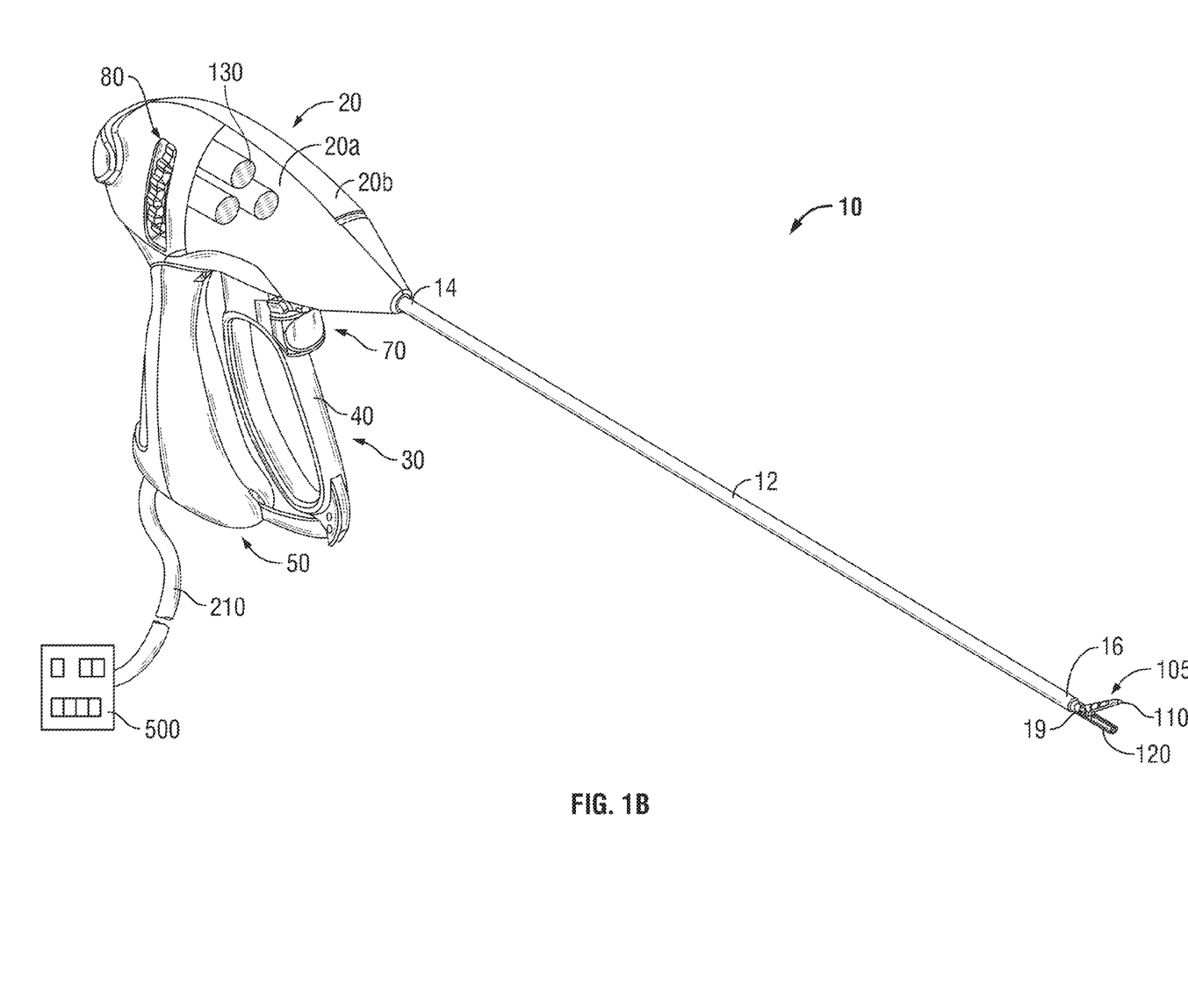
FIG. 1B is an internal view of the electrosurgical instrument of FIG. 1A.

FIG. 1B depicts an internal view of housing 20 according to an embodiment of the present disclosure. As shown in FIG. 1B, housing 20 includes a number of transducers 130 that are electrically coupled to generator 500 via conduit 210. Alternatively, generator 500 may be incorporated into housing 20. A battery pack (not shown) may also be included in housing 20 to supply energy to a generator disposed in housing 20. Although only three (3) transducers are depicted, any number of transducers may be used without departing from the scope of the present disclosure. Transducers 130 are acoustical transducers that convert electrical energy into acoustic waves. Transducer 130 may be a piezoelectric transducer that includes a piezoelectric ceramic element that creates and distributes ultrasonic sound waves. When a voltage is applied from generator 500 to transducer 130, piezoelectric material within transducer 130 will bend, stretch, or otherwise deform. This deformation is usually very slight and proportional to the voltage applied, and, as such, offers a method of precision movement on the micro scale. The voltage generated by a piezoelectric transducer can be quite high, often in the thousands of volts, but is brief, occurring only when the material is initially deformed. The piezoelectric material may include crystals (e.g., quartz or topaz) or polymers or ceramics that show piezoelectric properties.

Figure 2:
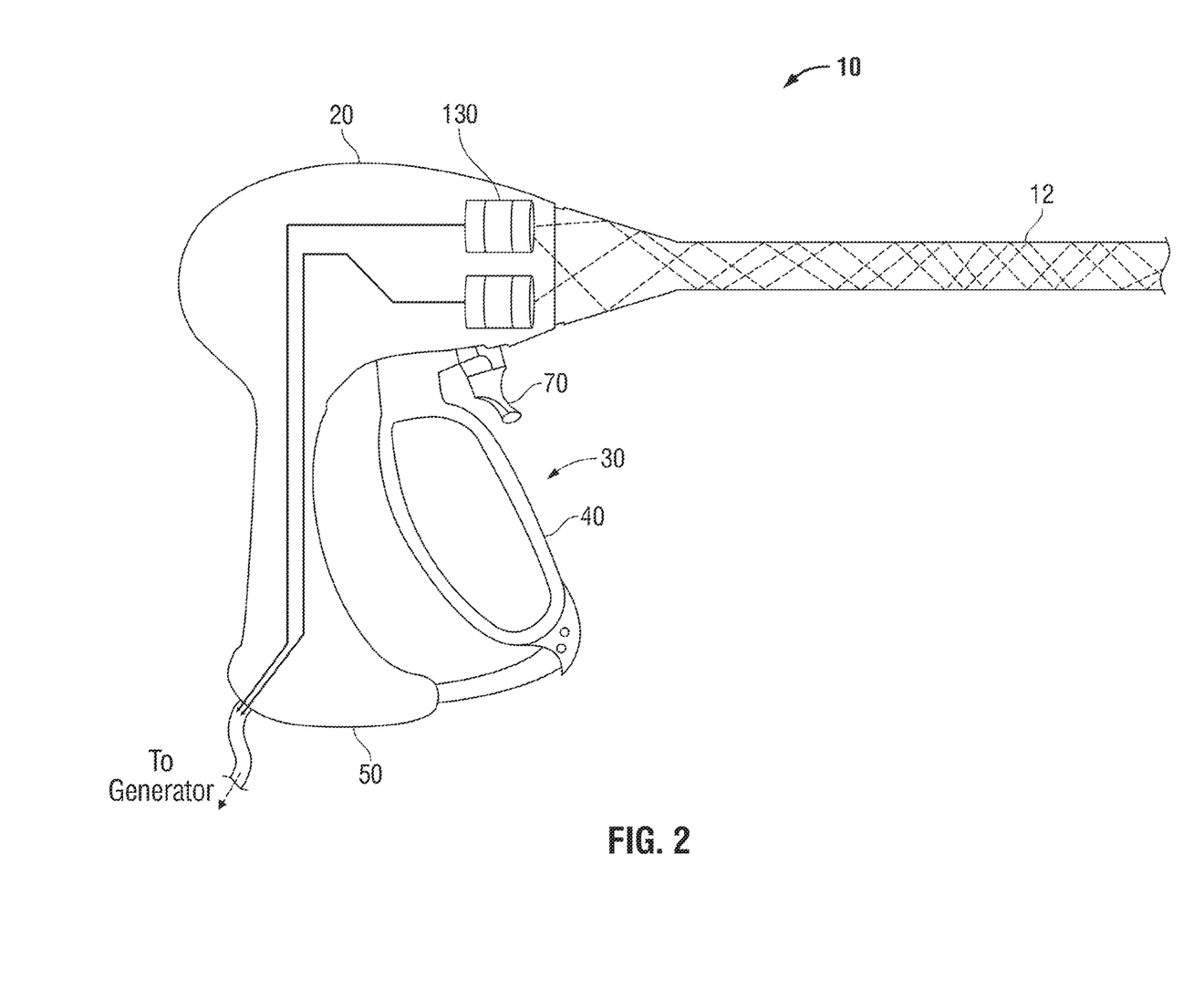
FIG. 2 is a schematic diagram of the electrosurgical instrument of FIG. 1A.
Figure 3:
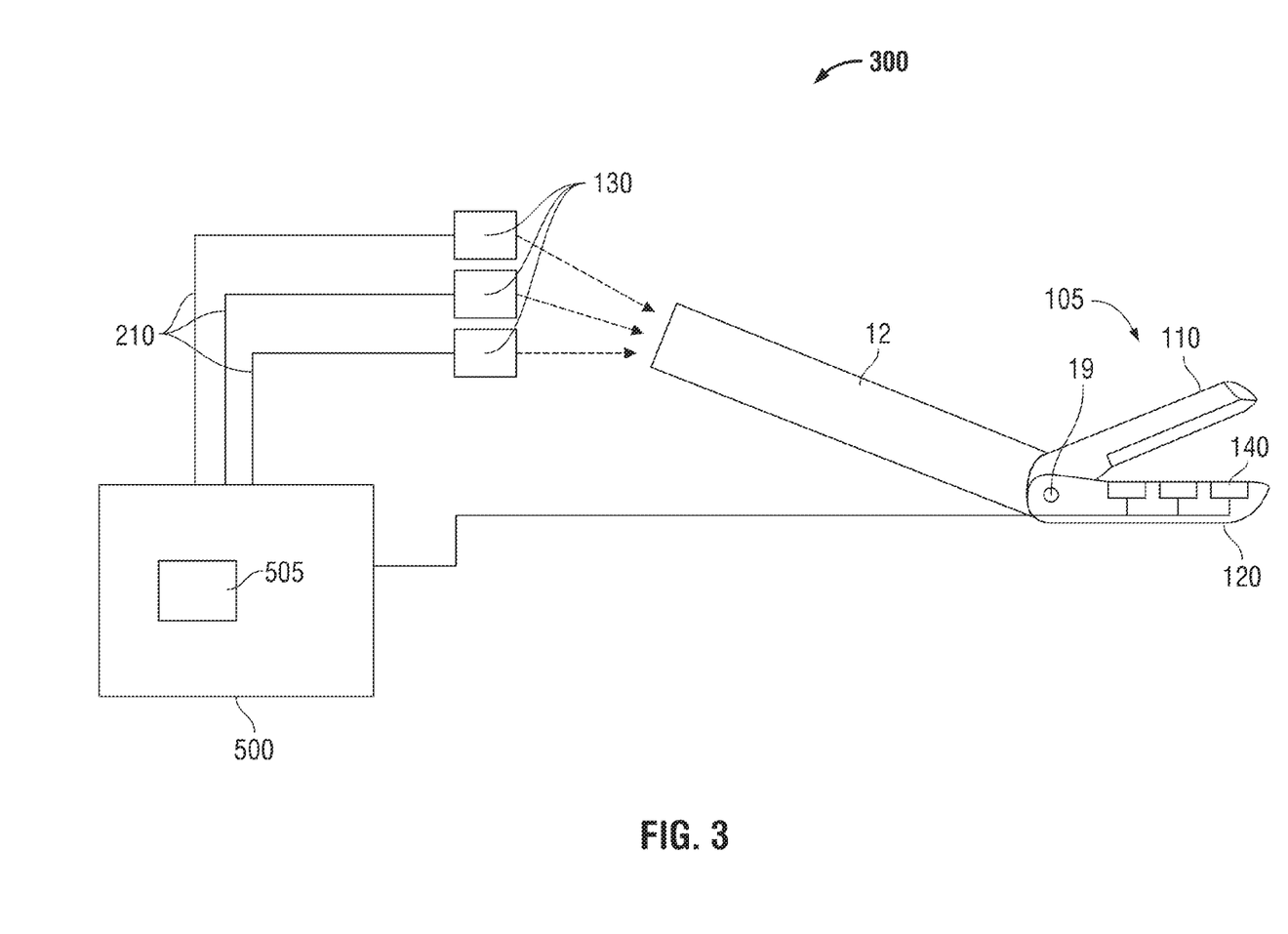
FIG. 3 is a schematic diagram of the electrosurgical instrument of FIG. 1A.
Figure 5:
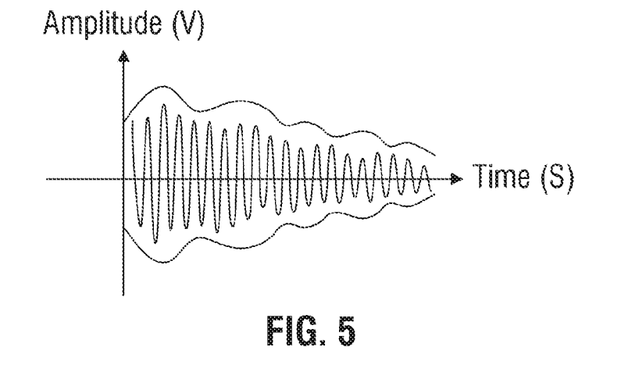
FIG. 5 is a graph depicting an electrical signal at the end effector assembly according to an embodiment of the present disclosure.

As shown in FIG. 2, transducers 130 generate acoustic waves, which propagate through the waveguide 12 to miniature piezoceramic probes 140 in end effector assembly 105 as shown in FIG. 3. Waveguide 12 is a solid metallic piece, e.g., aluminum, that transmits acoustic waves therethrough. The waveguide 12 does not vibrate. The acoustic waves undergo multiple reflections resulting in an electrical signal registered at the output of probe 140 as shown in FIG. 5.

FIG. 3 depicts a schematic diagram of the electrosurgical system according to an embodiment of the present disclosure. As shown in FIG. 3, the system 300 includes a generator 500. Generator 500 can perform ultrasonic electrosurgical procedures and may include a plurality of outputs for interfacing with various electrosurgical instruments (e.g., a monopolar active electrode, return electrode, bipolar jaw members, footswitch, ultrasonic horn, etc.). Further, generator 500 includes electronic circuitry configured for generating power specifically suited for various electrosurgical modes (e.g., cutting, blending, division, fragmenting, coagulating etc.) and procedures. Generator 500 includes suitable input controls (e.g., buttons, activators, switches, touch screen, etc.) for controlling the generator 500. In addition, the generator 500 may include one or more display screens for providing the user with variety of output information (e.g., intensity settings, treatment complete indicators, etc.). The controls allow the user to adjust power of the energy, waveform, as well as the level of maximum arc energy allowed that varies depending on desired tissue effects and other parameters to achieve the desired waveform suitable for a particular task (e.g., coagulating, tissue sealing, intensity setting, etc.). In another embodiment, generator 500 may be included in fixed handle 50 of handle assembly 30.

Generator 500 provides an electrical signal to transducers 130, which, in turn, generate acoustic waves or signals that are propagated through waveguide 12 to probes 140 in end effector assembly 105. Probes 140 are piezoceramic transducers that receive acoustic waves from transducers 130 and output the acoustic waves to tissue grasped between jaw members 110 and 120. Although FIG. 3 depicts probes 140 in lower jaw member 120, the probes 140 may be disposed in upper jaw member 110 and/or lower jaw member 120. Probes 140 are electrically coupled to generator 500 and transmit the electrical signal (FIG. 5) thereto.

Generator 500 includes a phase/time reversal unit (PRU) 505. PRU 505 performs time reversal signal processing that is a technique for focusing waves. Time reversal signal processing is based upon a feature of wave equations known as reciprocity. Reciprocity says that if one has a solution to the wave equation, then the time reversal (using a negative time) of that solution is also a solution of the wave equation. This occurs because the standard wave equation only contains even order derivatives. Time reversal techniques can be modeled as a matched filter that is included in the PRU 505.

Figure 6:
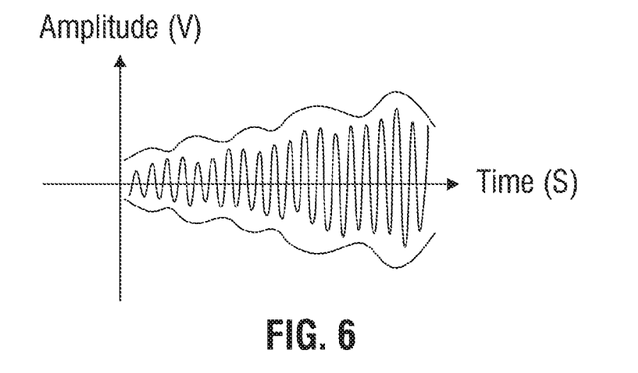
FIG. 6 is a graph depicting the electrical signal of FIG. 5 after processing by the phase/time reversal block according to an embodiment of the present disclosure.
Figure 7:
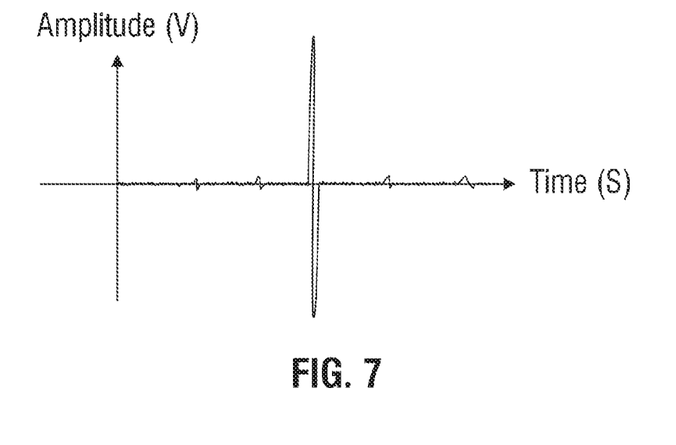
FIG. 7 is a graph depicting the resulting signal at a spot according to an embodiment of the present disclosure.

After probes 140 receive the acoustic signal from transducers 130, probes 140 transmit an electrical signal generated from the acoustic signal to the PRU 505. PRU 505 sends the reversed version (see FIG. 6) of the electrical signal of FIG. 5 to transducers 130 that transmit an acoustic signal back to probes 140 thereby, effectively autocorrelating the signal. Due to the principle of acoustical reciprocity, the reversed signal will be focused precisely in the same spot where it came from, i.e., probe 140. The resulting signal is concentrated in both time and space resulting in a signal that resembles a delta function as shown in FIG. 7. This precise focusing allows acoustic energy to be concentrated in a very small spot, thereby reducing thermal spread.

Using the inputs on generator 500, a clinician can select between sealing tissue grasped between jaw members 110 and 120 or cutting tissue between jaw members 110 and 120. A lower power setting may be used for sealing tissue while a higher power setting may be used to cut tissue. Using time reversal signal processing reduces the amount of energy needed (e.g., up to 5 times less energy) and eliminates the need for an amplifier, thereby reducing the components necessary in generator 500.

Figure 4A:
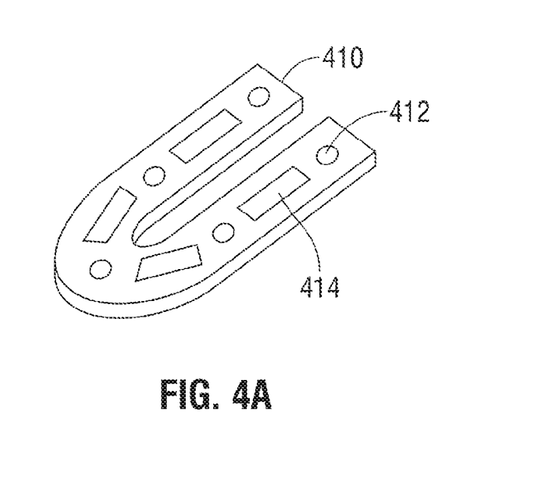
FIG. 4A-4C are perspective views of the end effector assemblies according to embodiments of the present disclosure.
Figure 4B:
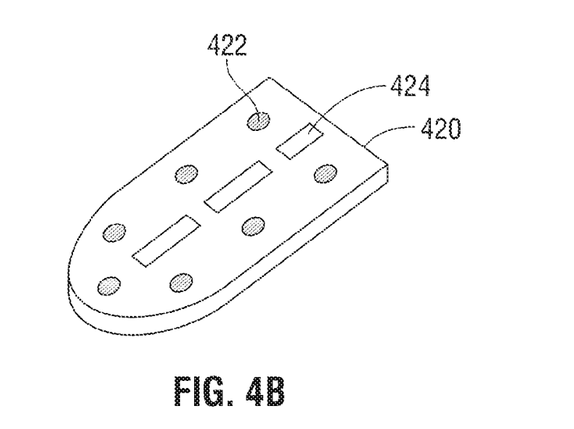

FIGS. 4A and 4B depicts different sealing surfaces for one of the jaw members of end effector assembly 105. As shown in FIG. 4A, sealing surface 410 includes a plurality of stop members 412 and piezoceramic transducers 414. Stop members 412 may provide a gap between jaw members 110 and 120 of end effector assembly 105 to effectively seal tissue. As shown in FIG. 4B, sealing surface 420 includes stop members 422 along the outer edges of sealing surface 420. Piezoceramic transducers 424 are disposed along the center of sealing surface 420. Transducers 414 and 424 may be formed beneath the sealing surfaces 410 and 420 respectively or be an integral part of sealing surface 410 and 420.

Figure 4C:
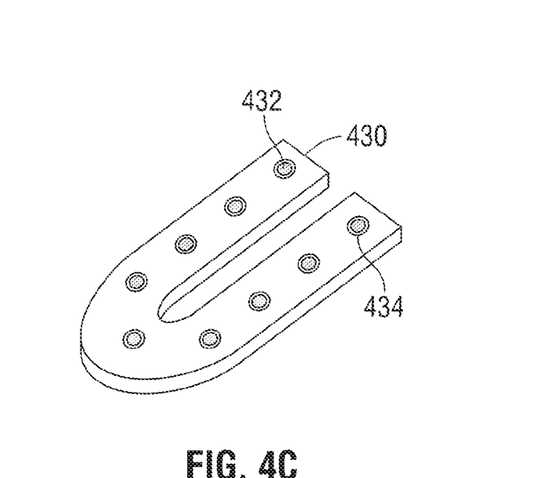

FIG. 4C depicts a top view of seal plate 430 according to another embodiment of the present disclosure. Seal plate 430 is made from stainless steel, and as described above, has piezoceramic transducers 432 disposed in locations 434 instead of stop members as shown in FIGS. 4A and 4B. Seal plate 430 may be formed by any suitable method. For instance, a layer of stainless steel may be provided and shaped to form seal plate 430. Then, a photolithography mask is applied to seal plate 430 leaving locations 434 exposed. An etching solution is applied to seal plate 430 to etch away exposed locations 434. Then the mask is removed leaving seal plate 430 with locations 434 etched away. When the jaw member is assembled, piezoceramic transducers 432 are placed in locations 434 of seal plate 430 and are coupled to generator 500.

The foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures. are presented only to demonstrate certain examples of the disclosure. Other elements, steps, methods and techniques that are insubstantially different from those described above and/or in the appended claims are also intended to be within the scope of the disclosure.

What is claimed is:

1. An electrosurgical instrument, comprising:
   a housing;
   a plurality of transducers disposed within the housing;
   a waveguide extending distally from the housing; and
   an end effector assembly supported by a distal portion of the waveguide, the end effector assembly including a first jaw member having a probe configured to both receive an acoustic signal from the plurality of transducers and output an electrical signal in response to receiving the acoustic signal, wherein the probe is configured to transmit the electrical signal to a generator.

2. The electrosurgical instrument according to claim 1, wherein the plurality of transducers is configured to receive a time-reversed single from the generator.

3. The electrosurgical instrument according to claim 2, wherein the plurality of transducers is configured to transmit the time-reversed signal to the probe through the waveguide.

4. The electrosurgical instrument according to claim 1, wherein the probe is a piezoceramic transducer.

5. The electrosurgical instrument according to claim 1, wherein the probe is disposed beneath a sealing surface of the first jaw member.

6. The electrosurgical instrument according to claim 1, wherein the probe is formed as an integral part of a sealing surface of the first jaw member.

7. The electrosurgical instrument according to claim 1, wherein the probe is formed as a stop member disposed on a sealing surface of the first jaw member.

8. A method of providing energy to tissue using an electrosurgical instrument including a housing, a plurality of transducers disposed within the housing, a waveguide extending distally from the housing, and an end effector assembly supported by a distal portion of the waveguide, the end effector assembly including a first jaw member having a probe, the method comprising:
   generating an acoustic signal with the plurality of transducers;
   receiving the acoustic signal with the probe; and
   converting the acoustic signal to an electrical signal with the probe.

9. The method according to claim 8, further comprising transmitting the acoustic signal through the waveguide with the plurality of transducers.

10. The method according to claim 8, further comprising:
   transmitting the electrical signal to a generator with the probe;
   processing the electrical signal in the generator to generate a time-reversed signal;
   receiving at the plurality of transducers the time-reversed signal;
   converting the time-reversed signal to a time-reversed acoustic signal with the plurality of transducers; and
   transmitting the time-reversed acoustic signal to the probe.

11. An electrosurgical instrument, comprising:
   a housing;
   a plurality of transducers disposed within the housing;
   a waveguide extending distally from the housing; and
   an end effector assembly supported by a distal portion of the waveguide, the end effector assembly including a first jaw member having a probe configured to both receive an acoustic signal from the plurality of transducers and output an electrical signal in response to receiving the acoustic signal, wherein the probe is a piezoceramic transducer.

12. An electrosurgical instrument, comprising:
   a housing;
   a plurality of transducers disposed within the housing;
   a waveguide extending distally from the housing; and
   an end effector assembly supported by a distal portion of the waveguide, the end effector assembly including a first jaw member having a probe configured to both receive an acoustic signal from the plurality of transducers and output an electrical signal in response to receiving the acoustic signal, wherein the probe is disposed beneath a sealing surface of the first jaw member.

13. An electrosurgical instrument, comprising:
   a housing;
   a plurality of transducers disposed within the housing;
   a waveguide extending distally from the housing; and
   an end effector assembly supported by a distal portion of the waveguide, the end effector assembly including a first jaw member having a probe configured to both receive an acoustic signal from the plurality of transducers and output an electrical signal in response to receiving the acoustic signal, wherein the probe is formed as an integral part of a sealing surface of the first jaw member.

14. An electrosurgical instrument, comprising:
   a housing;
   a plurality of transducers disposed within the housing;
   a waveguide extending distally from the housing; and
   an end effector assembly supported by a distal portion of the waveguide, the end effector assembly including a first jaw member having a probe configured to both receive an acoustic signal from the plurality of transducers and output an electrical signal in response to receiving the acoustic signal, wherein the probe is formed as a stop member disposed on a sealing surface of the first jaw member.

* * * * *